(12) United States Patent
Kishan et al.

(10) Patent No.: US 7,473,752 B2
(45) Date of Patent: Jan. 6, 2009

(54) FUNCTIONALIZED SILICONE RESINS, METHODS FOR THEIR PREPARATION, AND USE AS CATALYSTS

(75) Inventors: Gurram Kishan, Bangalore (IN); Rajappan Vetrivel, Bangalore (IN); Nileshkumar Prakash Kukalyekar, Sangli (IN); Adil Minoo Dhalla, Dadar Mumbai (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 11/702,464

(22) Filed: Feb. 5, 2007

(65) Prior Publication Data

US 2007/0135661 A1 Jun. 14, 2007

(51) Int. Cl.
*C08G 77/28* (2006.01)
(52) U.S. Cl. .............................. 528/30; 528/34; 528/35
(58) Field of Classification Search .................... 528/30, 528/34, 35
See application file for complete search history.

(56) References Cited

U.S. PATENT DOCUMENTS

| | | | |
|---|---|---|---|
| 4,054,552 A * | 10/1977 | Hoogeboom | ................ 528/167 |
| 4,217,438 A | 8/1980 | Brunelle et al. | |
| 4,552,700 A | 11/1985 | Panster et al. | |
| 5,789,628 A | 8/1998 | Auer et al. | |
| 5,919,566 A | 7/1999 | Lansink-Rotgerink et al. | |
| 6,229,037 B1 | 5/2001 | Okubo et al. | |

FOREIGN PATENT DOCUMENTS

| EP | 0 765 897 A2 | 4/1997 |
| EP | 0856 505 A1 | 8/1998 |

OTHER PUBLICATIONS

EP0765897; Apr. 2, 1997 Abstract Only (1 page).
EP0856505; Aug. 5, 1998 Abstract Only (1 page).

* cited by examiner

*Primary Examiner*—Kuo-Liang Peng

(57) ABSTRACT

Disclosed herein are silicone resins comprising structural units of the formula:

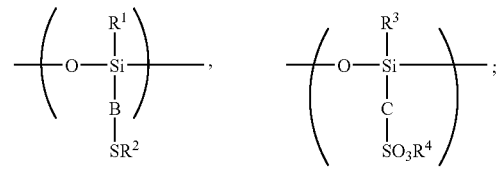

and
at least one structural unit selected from the group consisting of:

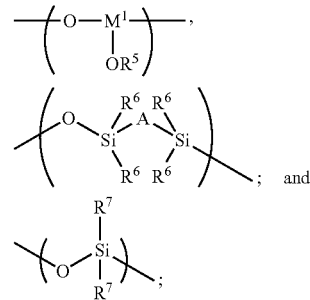

where "A" is a spacer group comprising $C_2$ to $C_{50}$ alkyl groups; "B" and "C" are spacer groups comprising $C_2$ to $C_{20}$ alkyl groups; "$M^1$" comprises a Group III element,; $R^1$, $R^3$, $R^6$, and $R^7$ independently comprise OH, alkyl groups, or alkoxy groups; $R^2$ and $R^4$ independently comprise hydrogen, alkali metal, or alkyl groups; and $R^5$ comprises a alkyl group. Methods for preparing these silicone resins are also disclosed. The silicone resins are useful as catalysts for producing bisphenols.

15 Claims, No Drawings

FUNCTIONALIZED SILICONE RESINS, METHODS FOR THEIR PREPARATION, AND USE AS CATALYSTS

BACKGROUND

This disclosure generally relates to functionalized silicone resin compositions and their use for the production of bisphenols. The disclosure further relates to methods for preparing these functionalized silicone resin compositions.

Bisphenols are valuable raw materials for producing polycarbonates. Polycarbonates are widely used in a variety of applications by virtue of their excellent physical properties, such as impact resistance, mechanical characteristics, transparency, and the like. Bisphenols are generally obtained by the reaction of a carbonyl compound with a phenol in the presence of an acidic catalyst, such as mineral acids or acidic ion exchange resins. One example of such acidic ion exchange resins is sulfonated polystyrene resin cross-linked with divinylbenzene, (PS-DVB). Frequently, a co-catalyst is used in conjunction with the acidic catalyst, to improve the selectivity for bisphenol such as the para, para-bisphenol isomer, for example. Co-catalysts can be present as unattached molecules in the bulk reaction matrix, e.g., "bulk co-catalysts", or can be attached to the acidic resin catalyst through ionic or covalent linkages. Mercaptans are one class of co-catalysts that can be employed. More specifically, thiols, e.g., organosulfur compounds derived from hydrogen sulfide, are used as co-catalysts. Numerous efforts have been made to improve the selectivity for bisphenols by varying the mercaptan co-catalyst and the acidic catalyst. One approach that has been attempted is to use a catalyst having an attached co-catalyst, which is prepared, for example, by reacting a portion of the acidic groups of the acidic ion exchange resins with aminomercaptans, to provide catalysts containing both mercaptan and sulfonic acid groups.

When ion exchange resin catalysts are used for making bisphenols by reaction of phenols with carbonyl compounds, the lifetime of the catalyst is affected by numerous factors, such as, for example, mechanical strength and fouling tendency. In addition, ion exchange resin catalysts typically include a pre-conditioning step, especially in continuous processes. Pre-conditioning is generally performed by passing the phenol through a packed bed of the ion exchange resin catalyst.

In view of these problems, there remains a need for alternative catalysts that have built-in functionalities for performing as a catalyst and a co-catalyst, and also allow for improved bisphenol selectivity, particularly for the para, para-bisphenol isomer. Furthermore, the alternative catalysts desirably have potentially superior mechanical properties as compared to the traditionally used ion-exchange resin catalysts, thereby leading to improved catalyst lifetime and bisphenol productivity.

BRIEF SUMMARY

Disclosed herein is a silicone resin comprising structural units of the formulae:

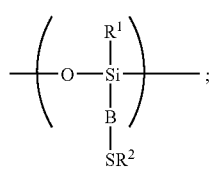 ; 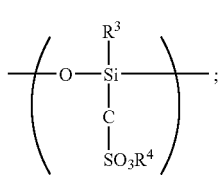 ;

and at least one structural unit selected from the group consisting of:

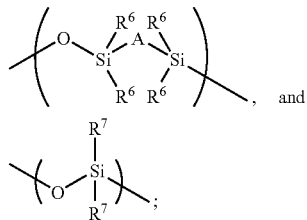, and where "A" is a spacer group comprising $C_2$ to $C_{50}$ alkylene groups; "B" and "C" are spacer groups comprising $C_2$ to $C_{20}$ alkylene groups, $R^1$, $R^3$, and $R^6$ independently comprise OH, alkyl groups, or alkoxy groups, $R^7$ comprises alkoxy groups; and $R^2$ and $R^4$ independently comprise hydrogen, alkali metal, or alkyl groups.

In another embodiment, a silicone resin consists essentially of structural units of the formulae:

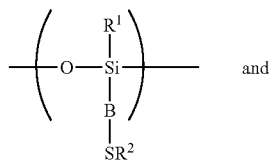 and

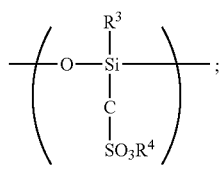 ;

where "B" and "C" are spacer groups comprising $C_2$ to $C_{20}$ alkylene groups, $R^1$ and $R^3$, independently comprise OH, alkyl groups, or alkoxy groups; and $R^2$ and $R^4$ independently comprise hydrogen, alkali metal, or alkyl groups.

A method of preparing a silicone resin comprises reacting a mercapto-functionalized alkoxysilane, an organosilyl sulfonic acid compound, and at least one reactant selected from the group consisting of a metal alkoxide compound, a bis(silyl) compound, and a poly(alkoxysiloxane) to produce a silicone resin comprising structural units of the formulae:

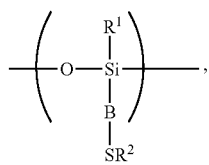, 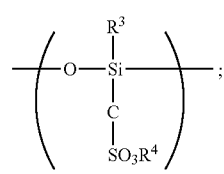 ;

and at least one structural unit selected from the group consisting of:

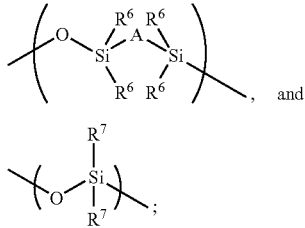, and where "A" is a spacer group comprising $C_2$ to $C_{50}$ alkylene groups; "B" and "C" are spacer groups comprising $C_2$ to $C_{20}$ alkylene groups; $R^1$, $R^3$, and $R^6$, independently comprise OH, alkyl groups, or alkoxy groups; $R^7$ comprises alkoxy groups; and $R^2$ and $R^4$ independently comprise hydrogen, alkali metal, or alkyl groups.

In another embodiment, a method of preparing a silicone resin, comprises reacting 1,4-bis(2-trimethoxyysilylethyl) benzene; 3 mercaptopropyltrimethoxysilane, 3-trihydroxysilylpropanesulfonic acid, and a metal alkoxide compound to produce a silicone resin comprising structural units of the formula:

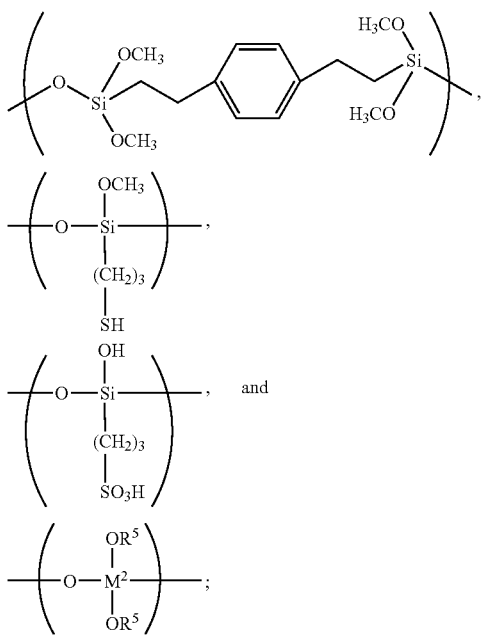

where $R^5$ independently comprises a alkyl group; and "$M^2$" is an element selected from the group consisting of silicon, titanium, and zirconium.

In still another embodiment, a method of producing an aromatic bisphenol comprises reacting a carbonyl compound with an aromatic hydroxy compound in the presence of a functionalized silicone resin catalyst; where the functionalized silicone resin catalyst comprises structural units of the formula:

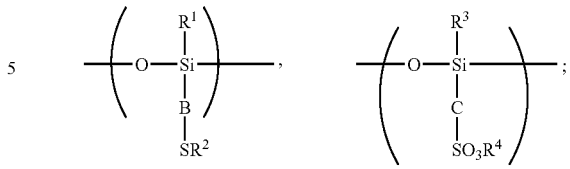

and at least one structural unit selected from the group consisting of:

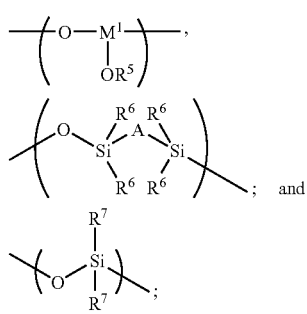; and where "A" comprises a $C_2$ to $C_{50}$ alkyl group; "B" and "C" independently comprise a $C_2$ to $C_{20}$ alkyl group; "$M^1$" comprises a Group III element; $R^1$, $R^3$, $R^6$, and $R^7$ independently comprise OH, alkyl groups, or alkoxy groups; $R^2$ and $R^4$ independently comprise hydrogen, alkali metal, or alkyl groups; and $R^5$ comprises a alkyl group.

The above described and other features are exemplified by the following detailed description. The various embodiments of the present disclosure have many advantages, including new silicone resin compositions, versatile methods for their preparation, and utility as a selective catalyst for producing bisphenols with high selectivity for para,para-bisphenols (also referred to as p,p-bisphenols).

DETAILED DESCRIPTION

A silicone resin suitable for catalyzing the reaction between a carbonyl compound and an aromatic hydroxy compound to produce an aromatic bisphenol includes structural units of formulas (I) and (II):

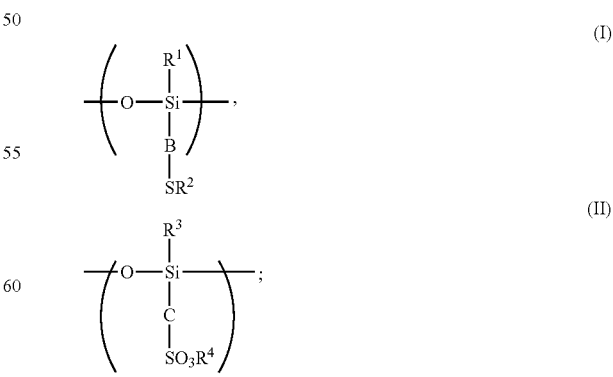

and at least one structural unit selected from the group consisting of formulae (IV) and (V):

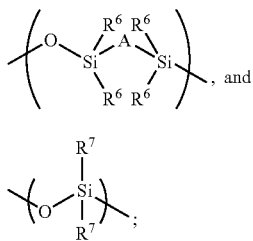

wherein "A" is a spacer group comprising $C_2$-$C_{50}$ alkylene groups; "B" and "C" are spacer groups comprising $C_1$-$C_{20}$ alkylene groups; $R^1$, $R^3$, and $R^6$, independently comprise OH, alkyl groups, or alkoxy groups; $R^7$ comprises alkoxy groups; and $R^2$ and $R^4$ independently comprise hydrogen, alkali metal, or alkyl groups. Advantageously, the silicone resin catalyst provides high selectivity relative to ion exchange resin catalysts.

The term "alkyl" as used herein is intended to designate straight chain alkyls, branched alkyls, aralkyls, cycloalkyls, and bicycloalkyl groups. The straight chain and branched alkyl groups, unless otherwise specified, are those containing about 1 to about 40 carbon atoms, and include as illustrative non-limiting examples methyl, ethyl, n-propyl, isopropyl, n-butyl, sec-butyl, tertiary-butyl, pentyl, neopentyl, hexyl, heptyl, octyl, nonyl, decyl, undecyl and dodecyl. In various embodiments, cycloalkyl groups represented are those containing about 3 to about 12 ring carbon atoms. Some illustrative non-limiting examples of these cycloalkyl groups include cyclobutyl, cyclopentyl, cyclohexyl, methylcyclohexyl, and cycloheptyl. In various embodiments, aralkyl groups are those containing about 7 to 14 carbon atoms; these include, but are not limited to, benzyl, phenylbutyl, phenylpropyl, and phenylethyl. In various other embodiments, aromatic groups used in the present disclosure are intended to designate monocyclic or polycyclic moieties containing about 6 to about 12 ring carbon atoms. These aryl groups may also contain one or more halogen atoms or alkyl groups substituted on the ring carbons. In most embodiments, any substituent present is not in a ring position that would prevent an appropriate aromatic group, such as in a phenolic aromatic group, from reacting with an appropriate olefinic group, such as in a monoterpene. Some illustrative non-limiting examples of these aromatic groups include phenyl, halophenyl, biphenyl, and naphthyl. In another embodiment, aromatic groups used in the present disclosure are intended to designate aralkyl groups containing about 7 to 14 carbon atoms.

The structural units of formula (I) are preferably derived from mercapto-functionalized alkoxysilanes of formula (VI):

$$R^2S-B-Si(OR^{11})_n(R^1)_{3-n} \tag{VI}$$

wherein "n" is an integer having values from 1 to about 3; $R^2$ comprises hydrogen, alkali metal, or a $C_1$ to $C_8$ alkyl group; and $R^1$ comprises OH, $C_1$ to $C_8$ alkyl groups, or $C_1$ to $C_8$ alkoxy groups. The spacer group "B" preferably comprises $C_2$ to $C_{20}$ alkylene groups, and more preferably, $C_2$ to $C_8$ alkylene groups. Non-limiting examples of the spacer group "B" include —($C_6H_4$)$CH_2$—, 1,2-ethylene, 1,3-propylene, 1,4-butylene, 1,5-pentylene, 1,6-hexylene, and 1,4-phenylene. $R^{11}$ comprises hydrogen, $C_1$ to $C_8$ linear and branched alkyl groups, or $C_1$ to $C_8$ linear and branched alkoxy groups. Non-limiting examples of mercapto-functionalized alkoxysilane of formula (VI) that lead to structural units of formula (I) include (3-mercaptopropyl)trimethoxysilane, (3-mercaptopropyl)triethoxysilane, (3-tert-butylmercaptopropyl)trimethoxysilane, (3-tert-butylmercaptopropyl)triethoxysilane, or mixtures of the foregoing alkoxysilanes. (3-mercaptopropyl)trimethoxysilane is particularly advantageous since it is commercially available.

Structural units of formula (II) are derived from an organosilyl sulfonic acid compound of formula (VII):

$$(SO_3R^4)-C-Si(OR^{12})_n(R^3)_{3-n} \tag{VII}$$

wherein "C" is a spacer group selected from the group consisting of $C_2$ to $C_{20}$ alkylene groups; $R^4$ comprises hydrogen, alkali metal, or $C_1$ to $C_8$ alkyl group, $R^3$ comprises OH, $C_1$ to $C_8$ alkyl group, or $C_1$ to $C_8$ alkoxy group; and $R^{12}$ independently comprises hydrogen, $C_1$ to $C_8$ alkyl groups, or $C_1$ to $C_8$ alkoxy groups. Non-limiting examples of the spacer group "C" include —($C_6H_4$)$CH_2$—, 1,2-ethylene, 1,3-propylene, 1,4-butylene, 1,5-pentylene, 1,6-hexylene, and 1,4-phenylene. In a preferred embodiment, the organosilyl sulfonic acid compound is selected from the group consisting of (3-trihydroxysilyl)propanesulfonic acid, (3-trimethoxysilyl)propanesulfonic acid, (3-triethoxysilyl)propanesulfonic acid, (4-trimethoxysilyl)phenylmethanesulfonic acid, and the corresponding ester derivatives of the foregoing sulfonic acids. The organosilyl sulfonic acids can be prepared by methods well known in the art. For example, (3-trimethoxysilyl)propanesulfonic acid can be prepared by oxidizing (3-mercaptopropanesulfonic acid with a suitable oxidizing agent, such as potassium permanganate in an appropriate solvent, such as acetone. (4-trimethoxysilyl)phenylmethanesulfonic acid can be prepared by treating (4-trimethoxysilyl)benzyl chloride with sodium sulfite in a solvent, such as ethanol, and stirring the reaction mixture overnight at a temperature of about 75° C. The resulting sodium (4-trimethoxysilyl)phenylmethanesulfonate is then treated with a strong acid, such as an acidic ion exchange resin to provide the desired (4-trimethoxysilyl)phenylmethanesulfonic acid. In a preferred embodiment, the organosilyl sulfonic acid compound comprises (3-trihydroxysilyl)propanesulfonic acid since it is commercially readily available, for example from Gelest Incorporated.

The structural units of formula (III) are generally derived from a metal alkoxide compound comprising a Group III element. More preferably, the structural units of formula (III) are generally derived from Group IIIB elements. Non-limiting examples of Group IIIB elements include boron, aluminum, and gallium. In a preferred embodiment, the metal alkoxide compound is selected from the group consisting of trimethyl aluminate, triethyl aluminate, tri(n-propyl)aluminate, tri(isopropyl)aluminate, tri(n-butyl)aluminate, tri(sec-butyl)aluminate, tri(tert-butyl)aluminate, and mixtures of the foregoing metal alkoxide compounds. Suitable metal alkoxide compounds also include those in which one or more of the alkoxy groups bonded to the metal in the metal alkoxide compounds may be the same, or they can all be different from one another.

The spacer group "A" in structural units of formula (IV) are generally derived from bis(silyl) compounds of the formula (VIII):

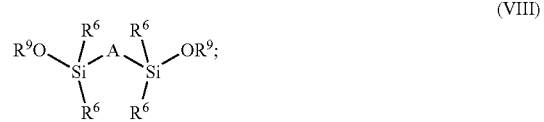

wherein $R^9$ independently comprises a hydrogen or an alkyl group; and wherein "A" and $R^6$ are as described above. In various embodiments, "A" is selected from the group consisting of —$(CH_2)_2$—, —$(CH_2)_8$—, and —$CH_2CH_2$—$(C_6H_4)$—$CH_2CH_2$—, and $R^9$ is selected from the group consisting of hydrogen, methyl, and ethyl, since the corresponding precursor compounds of formula (VIII) are either commercially readily available or can be prepared by methods known in the art.

The structural units of formula (V) can be derived from a variety of precursor materials. The $R^7$ groups present in formula (V) are preferably selected from the group consisting of OH, alkyl groups, or alkoxy groups. In a preferred embodiment, the $R^7$ groups are selected from the group consisting of $C_1$-$C_4$ alkoxy groups.

In an alternative embodiment, the structural units of formula (V) comprise polyalkoxysiloxane, as exemplified by compounds of the formula (IX):

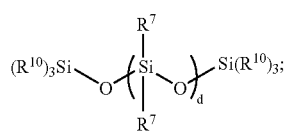

wherein $R^7$ and $R^{10}$ each independently comprises OH, $C_1$ to $C_8$ linear and branched alkyl groups, or $C_1$ to $C_8$ linear and branched alkoxy groups; and "d" represents the number of repeat units. More preferably, the $R^7$ group is a $C_1$ to $C_4$ alkoxy group. In a preferred embodiment, the polyalkoxysilanes comprise the polydialkoxysiloxane class of compounds. Non-limiting examples of suitable polydialkoxysiloxanes that generate the structural units of formula (V) include poly(diethoxysiloxane), poly(dimethoxysiloxane), poly(dipropoxy)siloxane, and the like polydialkoxysiloxanes. In a preferred embodiment, the poly(dialkoxysiloxane) comprises poly(diethoxy)siloxane having from about 20-30 weight percent of silicon. Commercially available poly(dialkoxy)siloxanes include, for example, those available from Gelest Inc., such as poly(dimethoxy)siloxane having a viscosity from about 6-9 centistokes, and about 26-27 weight percent silicon; poly(diethoxy)siloxane having a viscosity of about 4-5 centistokes, and about 20.5-21.5 weight percent silicon, and poly(diethoxy)siloxane having a viscosity of about 4-5 centistokes, and about 23-23.5 weight percent silicon.

Optionally, the silicone resin may further include a metal alkoxide structural unit of formula (X):

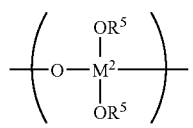

where $M^2$ is a Group IV element; and $R^5$ comprises hydrogen or an alkyl group. These metal alkoxide compounds are readily available either commercially or by methods well known in the art, such as for example, the TYZOR series of titanium alkoxy compounds available from DuPont. In a preferred embodiment, the metal alkoxide compound of formula (X) is selected from the group consisting of tetraethyl orthosilicate, tetramethyl orthosilicate, tetraisopropyl orthosilicate, tetraethyl orthotitanate, tetraethyl orthotitanate, tetramethyl orthotitanate, tetraisopropyl orthotitanate, tetramethyl orthozirconate, tetraethyl orthozirconate, tetrapropyl orthozirconate, tetra(isopropyl)zirconate, and mixtures of the foregoing tetraalkoxy metal compounds. Suitable metal alkoxide compounds also include those in which one or more of the alkoxy groups bonded to the metal in the metal alkoxide compounds may be the same, or they can all be different from one another.

Silicone resins comprising the structural units of formulas (I), (II), and at least one of the structural units of formulas (III) through (V), as described hereinabove, can be prepared by using the appropriate mercapto-functionalized alkoxysilane; organosilyl sulfonic acid compound; and a reactant comprising at least one reactant selected from the group consisting of the first metal alkoxide compound, a bis(silyl) compound, and a poly(alkoxysiloxane) compound. A wide variety of solvents can be used to prepare the silicone resins. Suitable solvents are those that comprise aliphatic alcohols, aromatic hydrocarbons, or mixtures of the foregoing solvents. In one embodiment, suitable solvents comprise $C_1$ to $C_5$ aliphatic alcohols, toluene, isomeric xylenes, or mixtures of the foregoing solvents. The process can be carried out in many ways based on the order of introduction of each ingredient into the reaction vessel. The reactions are carried out at a temperature from about ambient temperature to about 125° C. in one embodiment, and from about 60° C. to about 80° C. in another embodiment.

The method generally comprises reacting a first metal alkoxide compound (i.e., formula (III)) with an additional metal alkoxide compound, if present, in alcohol at about ambient temperature. The additional metal alkoxide is independently selected from the group consisting of Group III (i.e., formula (III)) and/or Group IV (i.e., formula (X)) metal alkoxides. Next, a solution of the mercapto-substituted alkoxysilane is added to the first metal alkoxide (or the product of the first metal alkoxide with the additional metal alkoxides) either neat, or as a solution and maintained at about ambient temperature, or pre-heated to a temperature from about 30° C. to about 125° C. An organosilyl sulfonic acid is then added to the resulting intermediate product solution followed by heating. The product is precipitated from the reaction mixture by addition of an anti-solvent, such as xylene. The precipitated solid is treated with an aqueous mineral acid, e.g., aqueous hydrochloric acid, and placed in an autoclave for a period of about 10 hours to about 24 hours. The final product is treated with de-ionized water until the washings are chloride-free. The resulting solid material is dried at a temperature from about 100° C. to about 150° C. under vacuum to give the final silicone resin.

An exemplary preferred silicone resin prepared in accordance with the methods described herein contains structural units compounds of formula (X), (XI), (XII), and (XIII):

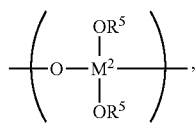

-continued

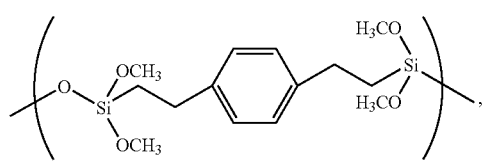 (XI)

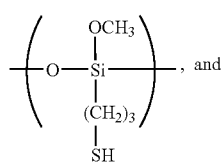 (XII), and

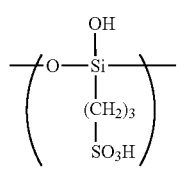 (XIII)

where $R^5$ independently comprises alkyl groups, and $M^2$ is selected from the group consisting of silicon, titanium, and zirconium.

The silicone resins are preferably prepared using separate building blocks having the sulfonic acid (or a corresponding derivative) and the mercaptan (or a corresponding derivative) groups. Optionally, silicone resins having both sulfonic acid or mercaptan type groups are prepared from a single precursor which has both the sulfonic acid and the mercaptan type groups. Non-limiting examples of such single precursors include compounds represented by the formulae (XIV)-(XVII):

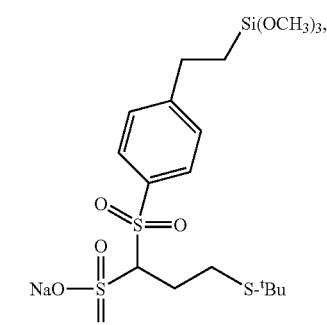 (XIV)

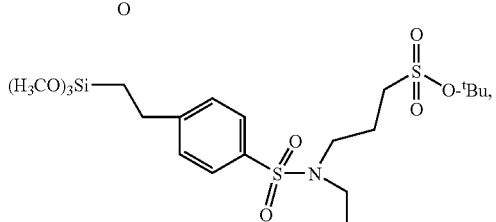 (XV)

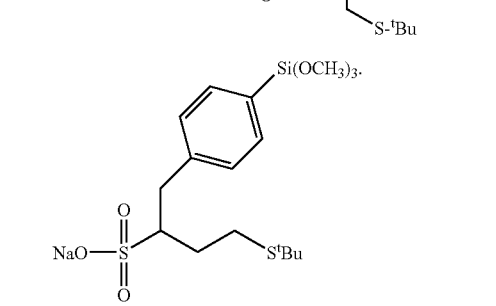 (XVI) and

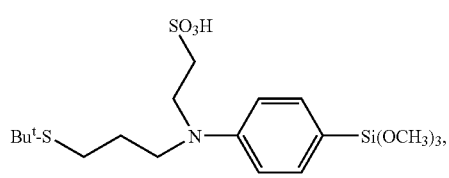 (XVII)

Various synthetic approaches can be used for preparing the precursors of formulae (XIV-(XVII)). For example, one approach for the synthesis of precursors of formulae (XV) and (XVI) is shown in Scheme 1. The method uses sodium 3-mercaptopropylsulfonate as the starting material. Alkylation at the sulfur position by using tert-butanol in the presence of hydrochloric acid or hydrogen chloride gas results in formation of (3-tert-butylmercaptopropyl)sulfonic acid. Next, (3-tert-butylmercaptopropyl)sulfonic acid is converted into isopropyl (3-tert-butylmercaptopropyl)sulfonate by a two step process. (3-tert-butylmercaptopropyl)sulfonic acid is first reacted with thionyl chloride to form (3-tert-butylmercaptopropyl)sulfonyl chloride, which is subsequently esterified with isopropanol to form isopropyl (3-tert-butylmercaptopropyl)sulfonate. Next, the (3-tert-butylmercaptopropyl) sulfonate is reacted with sodium hydride to form the corresponding carbanion caused by deprotonation adjacent to the sulfone group. Treatment of the carbanion with (4-trimethoxysilyl)methyl chloride gives the precursor of formula (XIV). Treatment of the carbanion with 4-(2-trimethoxysilylethyl)benzenesulfonyl chloride gives the precursor of formula (XV).

Scheme 1.

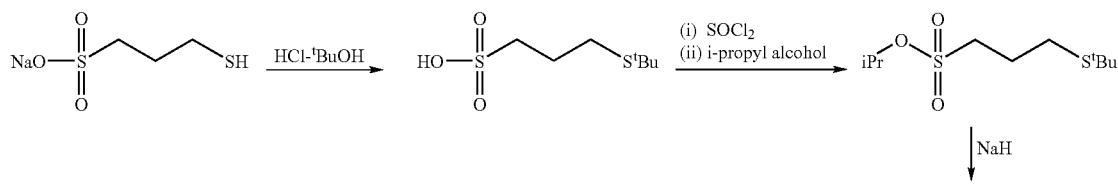

-continued

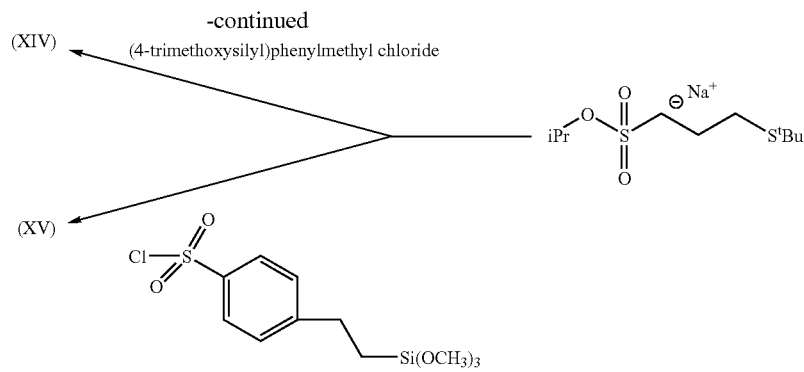

Preparation of other precursors can be prepared in accordance with Scheme 2. 3-(2-mercaptoethylamino)propanesulfonic acid is reacted with a tert-butylating agent so as to protect the reactive mercapto and sulfonic acid groups as the tert-butyl derivatives. The secondary amino group in the doubly protected intermediate product thus obtained is next reacted with a 4-(2-trimethoxysilylethyl)benzenesulfonyl chloride to afford the precursor of formula (XVI).

(hereinafter also sometimes referred to as aromatic hydroxy compounds). The silicone resins have both the acidic sulfonic acid group to accelerate the condensation reaction forming bisphenol, as well as the mercaptan group to provide enhanced selectivity for the p,p-bisphenol isomer.

Bisphenols are generally produced by reaction of a phenol with a carbonyl compound. For example, the silicone resins can effectively catalyze the reaction of phenol with acetone to

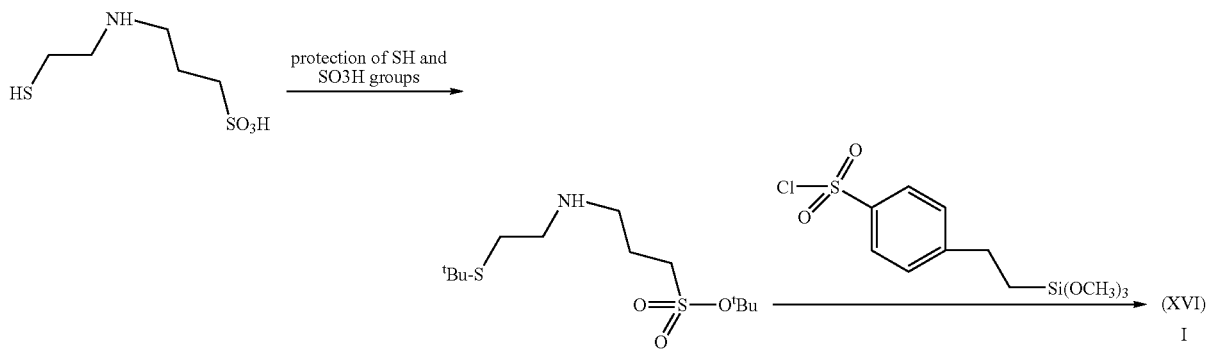

The precursors exemplified by the compound represented by formula (XVII) is synthesized by the route shown in Scheme 3. (4-aminophenyl)trimethoxysilane is N-alkylated with tert-butyl 3-bromopropyl sulfide to give the intermediate product as shown in Scheme 3. This intermediate is next reacted with a sultone compound, such as 1,3-propanesultone to result in the product of formula (XVII).

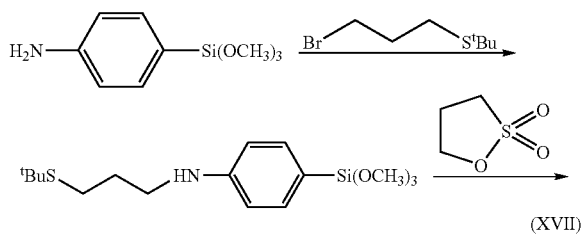

As previously discussed, the silicone resins described herein are valuable as catalysts for producing bisphenols produce bisphenol A. Any type of a carbonyl compound, such as aldehydes and ketones can be used for the condensation reaction with a phenol. The ketone starting materials may be commercial grade or better. As readily understood by one of ordinary skill in the art, commercial grade reagents may contain measurable levels of typical impurities such as aldehydes, acetophenone, benzene, cumene, diacetone alcohol, water, mesityl oxide, and methanol, among others. In one embodiment, suitable carbonyl compounds that can be used include at least one selected from the group consisting of acetone, methyl ethyl ketone, diethyl ketone, benzyl, acetyl acetone, methyl isopropyl ketone, methyl isobutyl ketone, acetophenone, ethyl phenyl ketone, cyclohexanone, cyclopentanone, benzophenone, fluorenone, indanone, anthraquinone, 4-hydroxyacetophenone, 4,4'-dihydroxybenzophenone, acenaphthenequinone, quinone, benzoylacetone diacetyl, fluorenone, bicyclo[2.2.1]heptan-2-one, and 3,3,5-trimethylcyclohexanone. Aldehydes such as for example, formaldehyde, acetaldehyde, propionaldehyde, butyraldehyde or higher homologues of the formula RCHO, wherein R is alkyl of 1-20 carbon atoms can also be used. The condensation of two moles of phenol with one mole of formaldehyde produces bis-(4-hydroxyphenyl)methane, also known as Bisphenol F. Any mixtures of the foregoing carbonyl compounds can also be used. The preferred carbonyl compound is acetone since it is a widely available and low cost material. Dialdehydes and ketoaldehdyes, such as for example, glyoxal, phenylglyoxal or pyruvic aldehyde, can also be used.

The aromatic hydroxy compound that can be used for producing the bisphenols can be a substituted or an unsubstituted aromatic compound containing at least one OH group. In one embodiment, suitable aromatic hydroxy compounds that can be used include, but are not limited to, at least one selected from the group consisting of phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6- xylenol, 2,6-dichlorophenol, 3,5-diethylphenol, 2-benzylphenol, 2,6-di-tertbutylphenol, 2-phenylphenol, 1-naphthol, and 2-naphthol. Any mixture of the foregoing aromatic hydroxy compounds can also be used. Phenol is a particularly valuable aromatic hydroxy compound that can be used for producing a variety of bisphenols, particularly bisphenol A by reaction with acetone.

The silicone resin can be used as catalysts for the reaction of the carbonyl compound with the aromatic hydroxy compound either in a batch or a continuous mode. In a batch mode, the carbonyl compound and the aromatic hydroxy compound are stirred in the presence of the silicone resin. The progress of the reaction is followed by techniques, such as gas chromatography or high-pressure liquid chromatography. In the continuous process of producing bisphenols (sometimes referred to as "aromatic dihydroxy compounds"), the carbonyl compound and the aromatic hydroxy compound are continuously introduced into at least one reactor comprising a fixed bed or fluidized bed packing comprising the silicone resin catalyst at an appropriate temperature. In one embodiment, the continuous process for making bisphenols is carried out in a single reactor packed with the silicone resin, where the phenol is passed continuously, and the carbonyl compound is introduced in one or more stages. The staged addition of carbonyl compound has the potential to offer improved selectivity for bisphenols. In particular, the staged addition of carbonyl compound may potentially improve the selectivity for the p,p-bisphenol isomer.

The feed comprising the phenol and the carbonyl compound is introduced to the silicone resin catalyst at a temperature from about 10° C. to about 200° C. Within this range, the introductory temperature is preferably greater than or equal to about 30° C., preferably greater than or equal to about 40 ° C., more preferably greater than or equal to about 45 ° C. Passing the feed through the silicone resin results in an effluent comprising the bisphenol, residual starting materials, water produced in the reaction, and various side products. The bisphenol produced (in the effluent) is predominantly para, para (p/p) bisphenol although some ortho, para (o/p) isomer is produced. The average ratio of p/p:o/p is preferably greater than or equal to about 20.

The bisphenol is then isolated from the residual starting materials, water and side products found in the effluent. In the isolation process, water, residual carbonyl compound and optionally some residual phenol are removed first, such as by vacuum distillation, to produce a bisphenol containing product stream. The removed carbonyl compound and residual phenol can be separated from the water and recycled to the reaction feed. The p/p bisphenol may then be isolated from the bisphenol containing product stream by methods known in the art, such as adduct crystallization, solvent crystallization, melt crystallization, distillation, or a combination of the foregoing isolation methods. The phenol compound removed from the product stream may be recycled for use in the catalyzed reaction or adduct crystallization when present. Advantageously, the high degree of selectivity of the reaction for p/p bisphenol results in the amount of impurities being greatly reduced, thus facilitating the isolation of the p/p bisphenol and improving the overall efficiency of the reaction and isolation.

In other embodiments of the continuous process, the single or multiple reactor system comprising the fixed bed packing of the catalyst may further comprise packing structures designed to alleviate the hydraulic stress that generally results from prolonged operation. Such packing structures may assume a variety of structures specially designed to withstand hydraulic stress, and may comprise materials inert to the reactive materials used for producing bisphenols. For example, the packing structures may comprise materials, such as steel, aluminum, ceramic, and the like. The silicone resin catalysts disclosed herein are generally expected to have crushing strengths comparable to other silicone resin catalysts disclosed in the art, and much higher than those reported for the traditionally used acidic ion exchange resin catalysts. Thus, the presence of the packing structures is expected to further improve the lifetime of the catalyst packing.

Aromatic dihydroxy compounds that can be prepared using the silicone resin catalysts described herein comprise those of the general formula (XVIII):

$$\text{HO-D}^2\text{-OH} \qquad (XVIII),$$

wherein $D^2$ is a divalent aromatic group.

In one embodiment, $D^2$ preferably has a structure as shown in formula (XIX):

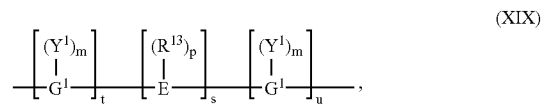

wherein $G^1$ represents an aromatic group, such as phenylene, biphenylene, naphthylene, and the like aromatic groups. E may be an alkylene or alkylidene group such as methylene, ethylene, ethylidene, propylene, propylidene, isopropylidene, butylene, butylidene, isobutylidene, amylene, amylidene, isoamylidene, and the like. Alternatively, E may consist of two or more alkylene or alkylidene groups connected by a moiety different from alkylene or alkylidene, such as an aromatic linkage, a tertiary amino linkage, an ether linkage, a carbonyl linkage, a silicon-containing linkage, a sulfur-containing linkage such as sulfide, sulfoxide, sulfone, a phosphorus-containing linkage such as phosphinyl, phosphonyl, and like linkages. In addition, E may comprise a cycloaliphatic group. $R^{13}$ represents hydrogen or a monovalent hydrocarbon group such as alkyl, aryl, aralkyl, alkaryl, cycloalkyl, and the like. $Y^1$ comprises a halogen (e.g., fluorine, bromine, chlorine, iodine, and the like); a nitro group; an alkenyl group, allyl group, the same as $R^8$ previously described, an oxy group such as OR, and the like. In a preferred embodiment, $Y^1$ is inert to and unaffected by the reactants and reaction conditions used to prepare the polymer. The letter "m" represents any integer from and including zero through the number of positions on $G^1$ available for substitution; "p" represents an integer from and including zero through the number of positions on E available for substitution; "t" represents an integer equal to at least one; "s" is either zero or one; and "u" represents any integer including zero.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, adamantylidene, etc.); a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy compound shown in Formula (XIX) when more than one $Y^1$ substituent is present, they may be the same or different. The same holds true for the $R^{13}$ substituent. Where "s" is zero and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ groups are unsubstituted phenylene groups; and E is an alkylidene group such as isopropylidene. In particular embodiments, both $G^1$ groups are p-phenylene, although both may be ortho- or metaphenylene or one ortho- or meta-phenylene and the other para-phenylene.

Some illustrative, non-limiting examples of aromatic dihydroxy compounds of formula (XIX) include the dihydroxy-substituted aromatic hydrocarbons disclosed by name or formula (generic or specific) in U.S. Pat. No. 4,217,438. Some particular examples of aromatic dihydroxy compounds include 4,4'-(3,3,5-trimethylcyclohexylidene)diphenol; 4,4'-bis(3,5-dimethyl)diphenol; 4,4-bis(4-hydroxyphenyl)heptane; 2,4'-dihydroxydiphenylmethane; bis(2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)ethane; 2,2-bis(4-hydroxyphenyl)propane (commonly known as bisphenol A); 2,2-bis(3-phenyl-4-hydroxyphenyl)propane; 2,2-bis(4-hydroxy-3-methylphenyl)propane; 2,2-bis(4-hydroxy-3-ethylphenyl)propane; 2,2-bis(4-hydroxy-3-isopropylphenyl)propane; 2,2-bis(4-hydroxy-3,5-dimethylphenyl)propane; 2,2-bis(3,5,3',5'-tetrachloro-4,4'-dihydroxyphenyl)propane; bis(4-hydroxyphenyl)cyclohexylmethane; 2,2-bis(4-hydroxyphenyl)-1-phenylpropane; 2,4'-dihydroxyphenyl sulfone; 2,6-dihydroxy naphthalene; hydroquinone; resorcinol; and $C_{1-3}$ alkyl-substituted resorcinols.

Bisphenols prepared in accordance with the methods described above are used in preparing polycarbonates. Polycarbonates are generally prepared by the polymerization reaction of an aromatic dihydroxy compound with a carbonate precursor, such as carbonyl halides or diaryl carbonates. Methods of polymerization include those disclosed in the art, such as interfacial polymerization, melt polymerization, solid-state polymerization, and solution polymerization.

The carbonate precursor is selected from the group consisting of phosgene, diphenyl carbonate, and diaryl carbonates substituted with one or more electron-withdrawing groups on one of both aromatic rings. Non-limiting examples of diaryl carbonates include those compounds where the aromatic rings are substituted with one or more of alkyl, halogen, chloro, bromo, fluoro, nitro, alkoxy, alkoxycarbonyl, methoxycarbonyl, ethoxycarbonyl, and cyano. Suitable diaryl carbonates include diaryl carbonates, dialkyl carbonates, and mixed aryl-alkyl carbonates, such as diphenyl carbonate, bis (2,4-dichlorophenyl) carbonate, bis(2,4,5-trichlorophenyl) carbonate, bis(2-cyanophenyl) carbonate, bis(o-nitrophenyl) carbonate, (o-carbomethoxyphenyl)carbonate; (o-carboethoxyphenyl)carbonate, ditolyl carbonate, m-cresyl carbonate, dinaphthyl carbonate, bis(diphenyl) carbonate, diethyl carbonate, dimethyl carbonate, dibutyl carbonate and dicyclohexyl carbonate, and combinations of two or more thereof. In an embodiment, the carbonate precursor is selected from the group consisting of phosgene, diphenyl carbonate, and bis(methylsalicylyl)carbonate. Two or more of these diaryl carbonates may also be utilized for preparing the polycarbonates. The aromatic dihydroxy compound comonomers described above may be used alone, or as mixtures of two or more different aromatic dihydroxy compound comonomers.

Melt polymerizations are generally carried out in the absence of a solvent and in the presence of a catalyst that facilitates the transesterification process. Non-limiting examples of such catalysts include alkali metal compounds, alkaline earth metal compounds, tetraorganoammonium compounds, and tetraorganophosphonium compounds.

Melt polymerization can be accomplished in a process involving one or more stages. The one stage process comprises manufacturing polycarbonates by melt polycondensation of the aromatic dihydroxy compound comonomer and the diaryl carbonate in the presence of the catalysts described above. The reactor employed can be made either of glass or a metal. Optionally, the reactor walls are passivated by treatment with a suitable acidic material. If it is desirable to carry out the polymerization in a glass reactor, soaking the glass reactor in an aqueous acid medium can be used to passivate the walls of the reactor. In various embodiments, the acids for this passivation process include water solutions of mineral acids, such as hydrochloric acid, sulfuric acid, nitric acid, and the like, and organic acids, such as acetic acid, methanesulfonic acid, toluenesulfonic acid, and the like.

The reactants for the polymerization reaction can be charged into the reactor either in a solid form or in a molten form. Initial charging of reactants into the reactor and subsequent mixing of these materials under reactive conditions for polymerization is preferably conducted in an inert gas atmosphere, e.g., a nitrogen atmosphere. Mixing of the reaction mixture is accomplished by methods known in the art, such as by stirring. Reactive conditions in the present context refer to conditions comprising time, temperature, pressure and other factors that result in polymerization of the reactants.

The polymerization is conducted by subjecting the above reaction mixture to a series of temperature-pressure-time protocols. For example, the reaction temperature may be gradually raised in stages while simultaneously gradually lowering the pressure in stages. Preferably, the pressure is about atmospheric pressure at the start of the reaction to, between about atmospheric pressure and about 0.01 millibar pressure, with between about atmospheric pressure and about 0.05 millibar pressure more preferred, and with between about 300 millibars pressure and about 0.05 millibar pressure even more preferred. The temperature is preferably varied to between about the melting temperature of the reaction mixture and about 350° C., with between about 180° C. and about 230° C. more preferred, with between about 230° C. and about 270° C. even more preferred, and with between about 270° C. and about 350° C. most preferred. This procedure will generally ensure that the reactants react properly to produce polycarbonates with a desired molecular weight, a desired glass transition temperature, and other desired physical properties. The reaction proceeds to build the polymer chain with production of phenol by-product. Efficient removal of the phenol by-product by application of vacuum can be used to produce polycarbonates of high molecular weight. If phenol is not removed efficiently, the phenol may undesirably cleave the growing polymer chain in the presence of the polymerization catalyst, thus leading to polymer of lower molecular weight. The reaction may be monitored by measuring the melt viscosity or the weight average molecular weight of the reaction mixture. After the desired melt viscosity and/or molecular weight is reached, the final polycarbonate product may be isolated from the reactor in a solid or molten form.

The method of producing polycarbonates can be operated either in a batch, semi-batch, or a continuous mode. Any reaction apparatus known in the art may be used in conducting this reaction.

The interfacial polymerization is carried out in at least one halogen-containing solvent by reacting phosgene and at least one aromatic dihydroxy compound comonomer of the formula (XVIII) in the presence of a suitable monohydric phenol, such as phenol, 4-cumylphenol, and the like as a chain-stopper. The solvent used for conducting the interfacial polymerization comprises at least one halogen-containing solvent. Examples of suitable solvents that can be used include, but are not intended to be limited to, dichloromethane, 1,1-dichloroethane, 1,2-dichloroethane, chlorobenzene, and the like. Carbon disulfide can also be used as a solvent. The chlorinated aliphatic hydrocarbons, especially methylene chloride, are preferred. The alkali metal hydroxide is necessary for adjusting the pH at an initial reaction stage as well as throughout the course of the polymerization reaction. Generally, the alkali metal hydroxide is introduced into the polymerization charge and the reaction mixture as an aqueous solution. Alternatively, water and the solid form of alkali metal hydroxide can also be used. Preferably, the alkali metal hydroxide is sodium hydroxide, potassium hydroxide, and combinations comprising at least one of the foregoing alkali metal hydroxides. The quantity of phosgene that needs to be introduced into the polymerization reactor to achieve complete conversion of the aromatic dihydroxy compound comonomer can vary from about a stoichiometric amount to about a 50 mole percent excess relative to the total number of moles of the aromatic dihydroxy compound comonomer, with about a 30 mole percent in excess more preferred.

Alternatively, the interfacial method of preparing polycarbonates can also be accomplished by first converting the dihydroxy aromatic compound to a bischloroformate, followed by reaction of the bischloroformate with an aromatic dihydroxy compound comonomer composition.

Advantageously, the silicone resin catalysts described in this disclosure are useful for producing a variety of bisphenols in high yield and selectivity. Moreover, as discussed above, the silicone resin catalysts can be prepared by simple methods using readily available starting materials. The bisphenols thus obtained are valuable for producing polycarbonates compositions, which in turn are useful for making various articles useful for high heat, optical, and engineering applications.

The following examples are presented for illustrative purposes only, and are not intended to limit the scope of the disclosure.

EXAMPLES

The following abbreviations are used to describe the various reactants used for preparing the silicone resin catalysts, referred to hereinafter as Cat-1-Cat 16. Table 1 provides a summary of the various catalysts and the structural units employed.

TEOS: Tetraethylorthosilicate; MPTES: (3-mercaptopropyl)triethoxysilane; TSPS: (3-trihydroxysilyl)propanesulfonic acid; BTSEB: 1,4-bis(2-trimethoxysilylethyl)benzene; MPTMS: (3-mercaptopropyl)trimethoxysilane; ZP: Zirconium(IV) isopropoxide; DBATS: Di-sec-butoxy aluminoxy triethoxysilane; BTESO: 1,8-bis(triethoxysily)octane; BTESE: 1,2-bis(triethoxysilyl)ethane; and PDEOS: Poly(diethoxysiloxane); PDMOS: Poly(dimethoxysiloxane).

Comparative Example 1

This Example describes the preparation of a prior art silicone resin catalyst, Cat-1.

In a three neck round bottom flask was taken TEOS (16.4 grams) and allowed to "condense", whereby it was allowed to stand overnight at ambient atmosphere to allow the slow hydrolysis of TEOS. To this material was added MPTES (5.82 grams) followed by 6.1 milliliters of ethanol. The resulting solution was stirred under reflux for about three hours, cooled to about 70° C., and treated with TSPS (8.3 milliliters of 30 percent by weight solution in water) and 16.2 milliliters of water. After the addition was complete, the resulting mixture was cooled to about 63° C., stirred for about 2 hours, and treated with about 71 milliliters of xylene. The resulting mixture turned into a thick white liquid that separated into two phases. After being heated for about 2 hours, small spherical particles of a white solid resulted in the two-phase system. The organic phase was separated, and the remaining portion was washed with deionized water to remove xylene, treated with 2 normal hydrochloric acid (35 milliliters), and the resulting mixture was transferred to a Teflon® autoclave and placed in an oven maintained at 150° C. for about 16 hours. The autoclave contents were cooled, filtered, the resulting solid product was washed with water until the water filtrate was chloride-free solution, then with ethanol to remove any unreacted organic material, and dried in a vacuum oven at about 130° C. for about 16 hours to furnish Cat-1 as a white powder.

Example 1

This Example describes the preparation of the catalyst Cat-2.

In a three-necked round-bottomed flask BTSEB was taken and allowed to "condense", whereby it was allowed to stand overnight at ambient atmosphere to allow the slow hydrolysis BTSEB, following which MPTES (9.7 grams) and ethanol (10 milliliters) was added. The resulting solution was stirred with an overhead stirrer and heated under reflux for about three hours, and then cooled to about 70° C. To the resulting solution was added with stirring, a 30 weight percent aqueous solution of TSPS (12.3 milliliters) and 15 milliliters of water, pre-heated to a temperature of about 70° C. The reaction mixture showed an exotherm, as seen by the rise of the temperature to about 75° C. After addition was complete, the reaction mixture was cooled to 63° C., and then stirred for about 2 hours. To the resulting mixture was then added xylene (71 milliliter) leading to the formation of a thick white solution. After being heated for about 2 hours, small white spherical particles were observed. The organic phase was separated, and the remaining aqueous portion was washed with sufficient deionized water to remove xylene, and treated with 35 milliliters of 2 Normal hydrochloric acid. The resulting material was transferred into a Teflon® autoclave and placed in an oven maintained at about 150° C. After about 16 hours, the autoclave is cooled to ambient temperature, and the contents were filtered. The resulting solid product was washed with water until the water washings were free of chloride ions, then washed with ethanol to remove water and any unreacted material, and finally dried in a vacuum oven at 130° C. for about 16 hours to furnish the silicone resin catalyst as a white powder.

Examples 2-11, 13, and 14

These Examples relate to preparation of the catalysts, Cat-3 to Cat-12, Cat-14, and Cat-15 using the procedure described above for preparing Cat-1. The weight of the starting materials taken for each preparation is shown in Table 1. "NA" in the Tables denotes "Not Applicable".

Example 12

In this example, silicone resin catalyst, Cat-13 was prepared using PDEOS, MPTMS, and TSPS as reactants. In this case, the MPTS and TSPS were added separately but simultaneously to PDEOS.

A four-necked round-bottomed flask equipped with two addition funnels, reflux condenser, and an overhead stirrer was kept in an oil bath equipped for being electrically heated. PDEOS was charged into the round-bottomed flask and stirred at room temperature for about two hours. Then MPTMS and TSPS was each taken in water (50 milliliters) and charged in separate addition funnels. The flow rate of each reactant was adjusted such that the addition of both reactants was completed at about the same time. After addition was completed, the reaction mixture was treated with xylene (50 milliliters) and stirred for about 2 hours. Further work-up of the reaction mixture followed the same procedure as described above for Example 1. The catalyst product was obtained as a white powder.

All the catalysts were also analyzed using X-ray Diffraction (XRD) to determine if the catalysts had an amorphous structure. For example, XRD analysis of Cat-12 and Cat-13 showed that they were amorphous materials. TGA measurements were also carried out on all the catalyst samples prepared. The catalysts were generally found to be stable up to about 250° C. Decomposition of the catalyst, accompanied by weight loss generally started at about 275° C., where less than or equal to about 2 percent of the weight of the sample taken for the analysis decomposed.

Table 1 shows that the amount of percent of structural units of formula —$(OSiR^7R^7)$— as a function of the combined weight of all the starting materials—PDEOS or PDMOS, MPTMS or MPTES, and TSPS, which are used for making the silicone resin is approximately in a range from 36.3 percent to 38.7 percent. Catalytic performance of the silicone resins was carried out by employing them in the reaction of phenol with acetone, either in a batch or a continuous mode, as described below.

Examples 15-20, and Comparative Examples 2 and 3

In these examples, various silicone resins were analyzed for producing bisphenol in a batch mode. Comparative Example 3 used Lewatit K1131 ion exchange resin (available from Bayer Company) as the catalyst, and 3mercaptopropionic acid as the cocatalyst.

A 20-milliliter vial equipped with a gas-tight septum was charged with phenol (11.6 grams), the catalyst (0.6 gram, about 5 weight percent), and placed in an oil bath maintained at a temperature of about 75° C. Then acetone was injected into the vial via a gas-tight syringe so that it forms 4.5 weight percent of the reaction mixture. The time at which acetone was added corresponds to zero time, i.e., start of the reaction. The progress of the reaction was monitored by gas chromatography (GC) by taking aliquots of the reaction mixture at different time intervals. Sample preparation for GC analysis is carried out as follows.

A sample weighing about 50 milligrams is withdrawn from the vial and weighed accurately. Then 0.5 milliliter of acetonitrile followed by the addition of dioctyl phthalate (internal standard for GC analysis) was added. To a 0.2 milliliter sample of this solution was added 0.5 milliliter of a derivatizing solution containing bis(trimethylsilyl)acetamide (BSA) or bis(trimethylsilyl)trifluoroacetamide (BTSA). The derivatizing solution was prepared by mixing 50 milliliters of acetonitrile, 25 milliliters of acetone, and 25 milliliters of BSA or BTSA. The resulting solution was used for GC analysis to determine p,p-BPA selectivity with an experimental error in measurement of ±0.2% with a 99% confidence.

The weight percent of acetone was determined by treatment of the sample with hydroxylamine hydrochloride, followed by titration of the liberated HCl. The weight percents

TABLE 1

| Example | Silicone Resin Catalyst | PDEOS (grams) | PDMOS (grams) | TEOS (grams) | BTSEB (grams) | DBATS (grams) | BTESO (grams) | BTESE (grams) | ZP (grams of 30% solution in propanol) | MPTMS (grams) | MPTES (grams) | TSPS (milliliters of 30% aqueous solution) | Wt % of —$(OSiR^2R^2)$— in the silicone resin product |
|---|---|---|---|---|---|---|---|---|---|---|---|---|---|
| 1 | Cat-2 | NA | NA | NA | 14.9 | NA | NA | NA | NA | NA | 9.7 | 12.3 | NA |
| 2 | Cat-3 | NA | NA | 14.8 | NA | NA | NA | NA | 8.6 | 3.4 | NA | 8.2 | NA |
| 3 | Cat-4 | NA | NA | NA | NA | NA | NA | NA | NA | 5.9 | NA | 6.7 | NA |
| 4 | Cat-5 | NA | NA | NA | NA | NA | NA | NA | NA | 5.9 | NA | 22.0 | NA |
| 5 | Cat-6 | NA | NA | NA | NA | 10.0 | NA | NA | NA | NA | 5.8 | 8.2 | NA |
| 6 | Cat-7 | NA | NA | NA | NA | NA | NA | NA | NA | 3.9 | NA | 27.0 | NA |
| 7 | Cat-8 | NA | NA | NA | NA | NA | 11.4 | NA | NA | 9.7 | NA | 12.3 | NA |
| 8 | Cat-9 | NA | NA | NA | NA | NA | NA | 9.2 | NA | 9.7 | NA | 12.3 | NA |
| 9 | Cat-10 | 7 | NA | NA | NA | NA | NA | NA | NA | 9.7 | NA | 12.3 | 38.7 |
| 10 | Cat-11 | 14 | NA | NA | NA | NA | NA | NA | NA | 19.5 | NA | 24.7 | 38.6 |
| 11 | Cat-12 | 8.7 | NA | NA | NA | NA | NA | NA | NA | 12.2 | NA | 15.4 | 38.4 |
| 12 | Cat-13 | 8.7 | NA | NA | NA | NA | NA | NA | NA | 12.2 | NA | 15.4 | 38.4 |
| 13 | Cat-14 | 14 | NA | NA | NA | NA | NA | NA | NA | NA | 24.8 | 24.7 | 37.9 |
| 14 | Cat-15 | NA | 12.7 | NA | NA | NA | NA | NA | NA | 19.5 | NA | 24.7 | 36.3 | of para-para-BPA, ortho-para-BPA, phenol, and bisphenol impurities in a reaction mixture sample were determined by standard high-pressure liquid chromatography (HPLC), with an experimental error in measurement of ±0.2% with a 99% confidence. The para-para-BPA selectivity and para-para-BPA to ortho-para-BPA ratio (p,p/o,o) were then calculated using the observed weight percents. The p,p-BPA selectivity was expressed as the ratio of the measured weight of p,p-BPA divided by the total weight of all components detected by the measurement technique (GC or HPLC). The Quantitative determination of water in samples was carried out using Karl Fischer titration method. The p,p/o,p ratio was based on the measured weights of p,p-BPA and o,p-BPA using GC or HPLC techniques. The results obtained are shown in Table 2.

TABLE 2

| Example | Catalyst | Temp (° C.) | Time (hours) | p,p BPA:o,p BPA ratio | p,p-BPA selectivity |
|---|---|---|---|---|---|
| 2* | Cat-1 | 55 | 2 | 72.2 | 78.1 |
|  |  |  | 4 | 79.5 | 82.4 |
|  |  |  | 8 | 88.2 | 86.4 |
|  |  |  | 24 | 113.9 | 92.6 |
| 15 | Cat-2 | 55 | 2 | 41 | 85.4 |
|  |  |  | 4.5 | 37.8 | 87.4 |
|  |  |  | 10 | 35.7 | 91.1 |
|  |  |  | 27 | 36 | 92 |
| 16 | Cat-3 | 75 | 3 | 29.7 | 89.7 |
|  |  |  | 6 | 28.9 | 91.2 |
|  |  |  | 24 | 27.3 | 93.9 |
| 17 | Cat-4 | 75 | 8 | 30.5 | 92 |
|  |  |  | 16 | 31.9 | 94.2 |
|  |  |  | 24 | 31.7 | 94.7 |
|  |  |  | 32 | 30.4 | 95.1 |
| 18 | Cat-9 | 75 | 7 | 23.5 | 94.1 |
|  |  |  | 11 | 25.3 | 94.7 |
|  |  |  | 19 | 30.1 | 94.5 |
| 19 | Cat-10 | 75 | 4 | 20.5 | 93.3 |
|  |  |  | 8 | 25.7 | 93.6 |
|  |  |  | 16 | 30.7 | 93.6 |
|  |  |  | 20 | 33.4 | 94.6 |
| 20 | Cat-11 | 75 | 5 | 26.4 | 89.7 |
|  |  |  | 12 | 35.9 | 92 |

TABLE 2-continued

| Example | Catalyst | Temp (° C.) | Time (hours) | p,p BPA:o,p BPA ratio | p,p-BPA selectivity |
|---|---|---|---|---|---|
|  |  |  | 19 | 38.8 | 95.2 |
|  |  |  | 26 | 35.9 | 95.3 |
| 3* | Lewatit K1131 | 75 | 2 | 18.3 | 92.8 |
|  |  |  | 4 | 17.5 | 92.4 |
|  |  |  | 7 | 17 | 92.3 |
|  |  |  | 24 | 16.1 | 92.1 |

*Denotes Comparative Example.

Examples 21-36

In these examples, various silicone resins were analyzed for producing bisphenol in a continuous mode.

A 10 to 15 gram sample of the silicone resin catalyst was packed into a column and held in place by a combination of glass wool and sand. The column was surrounded by a water jacket maintained at a temperature of about 55 to about 75° C. A feed mixture comprising phenol and acetone, as shown in Table 3, was added to the top of the column. Addition of the feed was controlled by a pump so as to maintain a weight hour space velocity as indicated in Table 3. The effluent from the column was collected and analyzed by acetone titration, water titration and liquid chromatography.

The results obtained from the continuous runs with the various catalysts are shown in Table 3. The term "Conversion" refers to the percentage of acetone that has been consumed relative to the amount taken for the reaction. "WHSV" stands for "weight hourly space velocity". The ratio p,p/o,p refers to the ratio of the p,p-BPA to the o,p-BPA formed.

The data in Table 3 shows that the for a given catalyst, the p,p-BPA selectivity is generally not significantly affected when the reaction temperature is raised from about 65° C. to about 75° C. Unlike the ion exchange resins, the catalyst compositions disclosed herein do not swell in the reaction medium during the formation of the bisphenols.

TABLE 3

| Example | Catalyst | Acetone (Weight %) | Temp (° C.) | WHSV | p,p:o,p ratio | Conversion | p,p-BPA Selectivity |
|---|---|---|---|---|---|---|---|
| 4* | Cat-1 | 4.8 | 65 | 1 | 35.6 | 66.5 | 92.6 |
| 5* | Cat-1 | 4.8 | 75 | 1 | 35.0 | 50.4 | 93.4 |
| 21 | Cat-10 | 5 | 75 | 1 | 33.2 | 77.2 | 94.3 |
| 22 | Cat-10 | 4.9 | 65 | 1 | 39.6 | 49.7 | 93.7 |
| 23 | Cat-10 | 4.9 | 65 | 0.5 | 38.9 | 56.7 | 94.6 |
| 24 | Cat-10 | 4.8 | 75 | 0.50 | 32.7 | 64.3 | 94.8 |
| 25 | Cat-10 | 4.8 | 75 | 0.4 | 30.2 | 73.7 | 94.5 |
| 26 | Cat-10 | 4.6 | 65 | 0.4 | 37.6 | 62.3 | 95.2 |
| 27 | Cat-12 | 5 | 65 | 0.6 | 41.7 | 36.9 | 93.2 |
| 28 | Cat-12 | 5 | 75 | 0.6 | 33.8 | 43.4 | 93.2 |
| 29 | Cat-12 | 5 | 75 | 0.3 | 30.5 | 58.7 | 93.9 |
| 30 | Cat-12 | 5 | 65 | 0.3 | 35.2 | 64.9 | 94.5 |
| 31 | Cat-12 | 1.3 | 75 | 1 | 26.0 | 44.4 | 95.2 |
| 32 | Cat-12 | 1.3 | 65 | 1 | 30.6 | 31.5 | 95.8 |
| 33 | Cat-13 | 5 | 65 | 1 | 42.6 | 52.6 | 93.6 |
| 34 | Cat-13 | 5 | 75 | 1 | 36.3 | 57.7 | 93.9 |
| 35 | Cat-13 | 5 | 75 | 0.4 | 32.3 | 76.1 | 94.6 |
| 36 | Cat-13 | 5 | 75 | 0.4 | 35.6 | 67.8 | 94.6 |

*Denotes Comparative Example.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims. All Patents cited herein are incorporated herein by reference.

What is claimed is:

1. A method of producing an aromatic bisphenol, wherein said method comprises reacting a carbonyl compound with an aromatic hydroxy compound in the presence of a functionalized silicone resin catalyst; wherein said functionalized silicone resin catalyst comprises structural units of the formula:

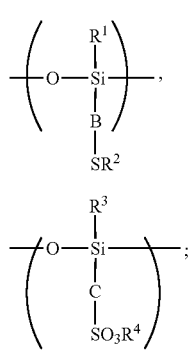

and
at least one structural unit selected from the group consisting of:

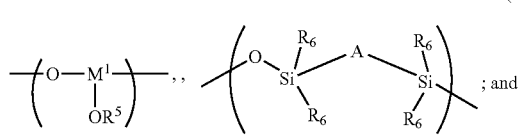

wherein the structural unit of formula (V), when present in the silicone resin without the structural unit of formula (IV), is present in an amount from 36.3 to 38.7 weight percent of overall weight of the silicone resin; and wherein "A" is spacer group that comprises a $C_2$ to $C_{50}$ alkylene group; "B" and "C" are spacer groups that independently comprise a $C_2$ to $C_{20}$ alkylene group; $R^1$, $R^3$, and $R^6$ independently comprise OH, alkyl groups, or alkoxy groups; $R^7$ comprises methoxy groups or ethoxy groups; and $R^2$ and $R^4$ independently comprise hydrogen, alkali metal, or alkyl groups.

2. The method of claim 1, wherein said carbonyl compound is at least one selected from the group consisting of acetone, methyl ethyl ketone, diethyl ketone, benzyl, acetyl acetone, methyl isopropyl ketone, methyl isobutyl ketone, acetophenone, ethyl phenyl ketone, cyclohexanone, cyclopentanone, benzophenone, fluorenone, indanone, anthraquinone, 4-hydroxyacetophenone, 4,4'-dihydroxybenzophenone, acenaphthenequinone, quinone, benzoylacetone diacetyl, fluorenone, bicyclo [2.2.1]heptan-2-one, and 3,3,5-trimethylcyclohexanone.

3. The method of claim 1, wherein said aromatic hydroxy compound is at least one selected from the group consisting of phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tertbutylphenol, 2-phenylphenol, 1-naphthol, and 2-naphthol.

4. The method of claim 1, wherein said carbonyl compound and said aromatic hydroxy compound are reacted in a batch or a continuous process.

5. The method of claim 4, wherein said continuous process comprises passing a feed-stream comprising said carbonyl compound and said aromatic hydroxy compound through at least one reactor packed with a fixed bed of said functionalized silicone resin catalyst.

6. The method of claim 4, wherein said continuous process comprises introducing said carbonyl compound in a staged addition to at least one reactor.

7. A method of making a polycarbonate from the bisphenol prepared in accordance with the method of claim 1.

8. The method of claim 7, wherein said aromatic bisphenol comprises bisphenol A or 1,1-bis(4-hydroxy-2-methylphenyl)cyclohexane.

9. The method of claim 1, wherein "A" is an alkylene group selected from the group consisting of $-(CH_2)_2-$, $-(CH_2)_8-$, and $-CH_2CH_2-(C_6H_4)-CH_2CH_2-$.

10. The method of claim 1, further comprising a structural unit having a formula:

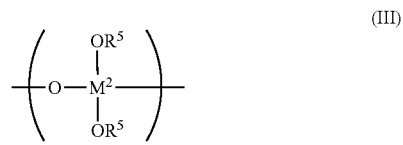

wherein $M^2$ comprises a Group IV element selected from the group consisting of titanium, silicon, and zirconium, and $R^5$ comprises hydrogen or an alkyl group.

11. The method of claim 1, wherein "B" and "C" are each independently an alkylene group selected from the group consisting of $-(CH_2)_2-$, $-(CH_2)_3-$, $-(C_6H_4)CH_2-$, and $-C_6H_4-$.

12. The method of claim 1, wherein the structural unit of formula (V) is derived from a polydimethoxysiloxane or a polydiethoxysiloxane.

13. A method of producing an aromatic bisphenol, wherein said method comprises reacting a carbonyl compound with an aromatic hydroxy compound in the presence of a functionalized silicone resin catalyst; wherein said functionalized silicone resin catalyst comprises structural units of the formula:

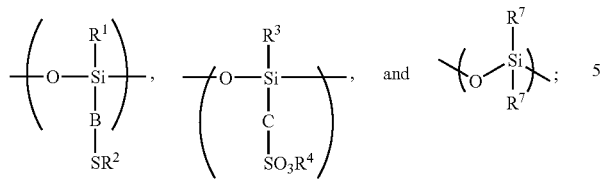

wherein the structural unit of formula

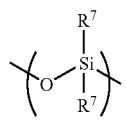

is present in the silicone resin in an amount from 36.3 to 38.7 weight percent of overall weight of the silicone resin; and wherein "B" and "C" are spacer groups that independently comprise a $C_2$ to $C_{20}$ alkylene group; $R^1$ and $R^3$ independently comprise OH, alkyl groups, or alkoxy groups; $R^7$ comprises methoxy groups or ethoxy groups; and $R^2$ and $R^4$ independently comprise hydrogen, alkali metal, or alkyl groups.

14. The method of claim 13 wherein the functionalized silicone resin catalyst further comprises structural units of the formula:

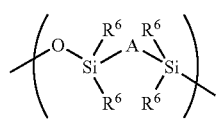

wherein "A" is a spacer group that comprises a $C_2$ to $C_{50}$ alkylene group; and $R^6$ independently comprise OH, alkyl groups, or alkoxy groups.

15. The method of claim 13 wherein the structural unit of formula

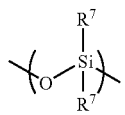

is derived from a polydimethoxysiloxane or a polydiethoxysiloxane.

* * * * *